United States Patent
Johnson

(10) Patent No.: US 6,878,119 B2
(45) Date of Patent: *Apr. 12, 2005

(54) METHOD FOR REDUCING ARTIFACTS IN A SPATIAL MEASUREMENT

(75) Inventor: Royce Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/197,139

(22) Filed: Jul. 17, 2002

(65) Prior Publication Data

US 2002/0183650 A1 Dec. 5, 2002

Related U.S. Application Data

(63) Continuation of application No. 09/780,767, filed on Feb. 9, 2001, now Pat. No. 6,682,491.
(60) Provisional application No. 60/181,731, filed on Feb. 11, 2000.

(51) Int. Cl.$^7$ .................................................. A61B 5/00
(52) U.S. Cl. ........................ 600/561; 600/587; 128/925
(58) Field of Search ................................. 600/480, 485, 600/500, 561, 587, 595; 128/920, 925

(56) References Cited

U.S. PATENT DOCUMENTS

| | | | | |
|---|---|---|---|---|
| 4,984,567 A | * | 1/1991 | Kageyama et al. | 600/438 |
| 5,431,170 A | * | 7/1995 | Mathews | 600/479 |
| 5,524,631 A | * | 6/1996 | Zahorian et al. | 600/511 |
| 6,231,509 B1 | * | 5/2001 | Johnson et al. | 600/438 |
| 6,385,471 B1 | * | 5/2002 | Mortz | 600/323 |
| 2003/0092999 A1 | * | 5/2003 | Goto et al. | 600/485 |

* cited by examiner

*Primary Examiner*—Max F. Hindenburg
*Assistant Examiner*—Jonathan Foreman

(57) ABSTRACT

A method for artifact reduction in sonomicrometer obtained intracranial pressure measurements generally comprises isolating a component of a sonomicrometer waveform attributable solely to changes in intracranial volume by using a neural network or other nonlinear engine to extract a heartbeat component from the sonomicrometer output. Because the heartbeat is so characteristic, no actual measurement of the heartbeat as the forcing function is required to isolate the resulting changes in distance from the artifact induced changes in distance. The neural network then be utilized to directly map measured changes in skull distance over time to changes in intracranial pressure over a volume change, the inverse of compliance. The method is generally extendable to use with other volumetric based measurement techniques.

4 Claims, 1 Drawing Sheet

METHOD FOR REDUCING ARTIFACTS IN A SPATIAL MEASUREMENT

RELATED APPLICATION INFORMATION

This application is a continuation of our application Ser. No. 09/780,767 entitled METHOD FOR ARTIFACT REDUCTION IN INTRACRANIAL PRESSURE MEASUREMENTS filed Feb. 9, 2001 now U.S. Pat. No. 6,682,491, which is incorporated herein by reference, and claims priority to provisional application Ser. No. 60/181,731, filed Feb. 11, 2000.

FIELD OF THE INVENTION

The present invention relates to artifact reduction. More particularly, the invention relates to a method for reducing artifacts in a spatial measurement.

BACKGROUND

It is known that a relative measure of intracranial pressure may be non-invasively obtained by measuring changes in a patient's skull diameter with a sonomicrometer or similar volumetric measurement type device. According to the known method, changes in the patient's skull diameter are directly related to changes in the patient's intracranial pressure. Because, however, the measured changes in skull diameter are extraordinarily small, indications of intracranial pressure obtained through this method are highly subject to vibration and/or slow drift artifacts. While vibration artifacts, such as may result from touching of the patient, may generally be removed from the estimate through simple low pass filtering, this is not the case for slow drift artifacts, such as may result from patient movements and the like. Slow drift artifacts are generally indistinguishable in the frequency domain from changes in intracranial pressure caused by edema, infectious process, tumor growth or bleeding. As a result, slow drift artifacts are generally very difficult to remove through standard filtering techniques.

It is therefore a primary object of the present invention to improve over the prior art by providing a method whereby slow drift type artifacts may be eliminated from the sonomicrometer obtained signals, thereby improving the quality of intracranial pressure measurement data derived therefrom. Although those of ordinary skill in the art will recognize that one such means for accomplishing this objective involves securing the sonomicrometer to the patient's skull with bone screws or the like, such a solution completely destroys the sonomicrometer's non-invasive character. As a result, it is a further object of the present invention to meet the primary object without sacrifice of the overall technique's non-invasive character.

SUMMARY OF THE INVENTION

In accordance with the foregoing objects, the present invention—a method for artifact reduction in sonomicrometer obtained intracranial pressure measurements—generally comprises isolating a component of a sonomicrometer waveform attributable solely to changes in intracranial volume by using a neural network or other nonlinear engine to extract a heartbeat component from the sonomicrometer output. Because the heartbeat is so characteristic, no actual measurement of the heartbeat as the forcing function is required to isolate the resulting changes in distance from the artifact induced changes in distance. The neural network can then be utilized to directly map measured changes in skull distance over time to changes in intracranial pressure over a volume change, the inverse of compliance.

According to the present invention a mapping from the sonomicrometer obtained distance measurements to an index of the mean intracranial pressure is obtained by using a neural network to examine only those components of the distance measurements corresponding to a known forcing function. According to the preferred implementation function, the known forcing function is chosen to be the heart beat waveform—a well-documented and highly characteristic waveform. By examining only those distance changes associated with the heart beat forcing function, artifacts associated with patient movement and the like are eliminated notwithstanding the fact that they may have fundamental frequencies corresponding to changes in intracranial pressure due to edema, infectious process, tumor growth and especially bleeding.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION

Although those of ordinary skill in the art will readily recognize many alternative embodiments, especially in light of the illustrations provided herein, this detailed description is exemplary of the preferred embodiment of the present invention, the scope of which is limited only by the claims which may be drawn hereto.

Figure 1:
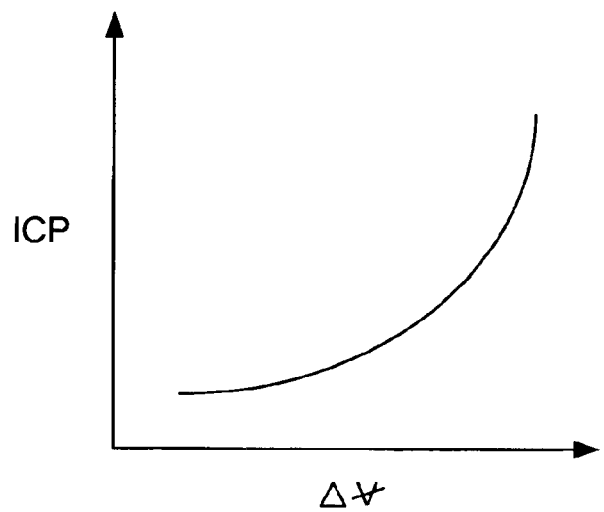
FIG. 1 shows a known relationship between changes in intracranial volume and intracranial pressure.

It is known that increases in intracranial pressure are normally buffered by the displacement of blood and cerebrospinal fluid from the cranium when there is an increase in intracranial volume, such as from edema, infectious process, tumor growth, bleeding or the like. This displacement, however, is limited by the total compliance of the bone and tissue forming the cranium. As depicted in the elastance curve of FIG. 1, as the intracranial volume approaches the capacity of the cranium, the compliance of the bone and tissue decreases and the intracranial pressure rises at an increasingly greater rate. Considering this relationship in reverse, therefore, it may be postulated that as the mean intracranial pressure increases, the effect on cranial compliance of a change in intracranial volume will be less and less profound. As a result, if a component of a sonomicrometer obtained distance waveform can be isolated from the artifacts within the waveform and attributed solely to a change in intracranial volume, then that isolated component may be relied upon as the basis for a measure of cranial compliance. Although not an absolute measure of intracranial pressure, the resulting compliance index can nonetheless be a very useful relative measure of the patient's physiology.

Figure 2:
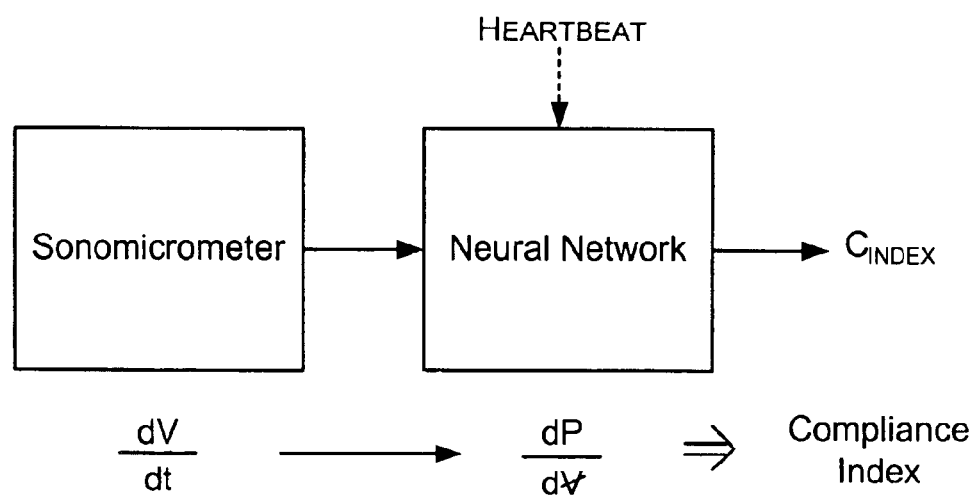
FIG. 2 shows an implementation according to the present invention for extracting a measure of intracranial compliance from a sonomicrometer output.

Referring now to FIG. 2, there is shown depicted one such means for isolating a component of a sonomicrometer waveform attributable solely to changes in intracranial volume. According to the method of the present invention, neural network or other nonlinear engine is used to extract a heartbeat component from the sonomicrometer output. Because the heartbeat is so characteristic, no actual measurement of the heartbeat as the forcing function is required to isolate the resulting changes in distance from the artifact induced changes in distance. A neural network, or the like, may be implemented to directly map measured changes in skull distance over time to changes in intracranial pressure over a volume change, the inverse of compliance.

Further, it is thought that the resulting compliance index may eventually be mapped to absolute measures of mean intracranial pressure according to key indicators to be discovered in the compliance index waveform. In particular, because the compliance index is a function of intracranial pressure, intracranial pressure may be estimated based upon a measured compliance index. The end result is an estimate of intracranial pressure derived from pulsatile changes in skull dimension and the knowledge of the intracranial pressure to compliance index relationship.

While the foregoing description is exemplary of the preferred embodiment of the present invention, those of ordinary skill in the relevant arts will recognize the many variations, alterations, modifications, substitutions and the like as are readily possible, especially in light of this description and the accompanying drawings. In any case, because the scope of the present invention is much broader than any particular embodiment, the foregoing detailed description should not be construed as a limitation of the scope of the present invention, which is limited only by the claims that may be drawn hereto.

I claim:

1. A method of artifact reduction in intracranial pressure measurements comprising isolating the change in distance attributable to changes in intracranial volume by extracting a heartbeat component from the measurements utilizing a neural network to map measured changes in skull distance over time.

2. The method according to claim 1 wherein changes in intracranial pressure over time are compared to changes in skull distance.

3. A method of artifact reduction in a spatial measurement of a cranium, comprising the steps of:

isolating a first component of the spatial measurement from a second, artifact-induced component of the spatial measurement by extracting components of the spatial measurement that correspond to a heart beat waveform; and mapping measured changes in skull distance over time to changes in intracranial pressure over a volume change.

4. The method of claim 3, wherein a neural network is used to isolate the first component from the second, artifact-induced component.

* * * * *